(12) United States Patent
Rak

(10) Patent No.: US 12,187,627 B1
(45) Date of Patent: Jan. 7, 2025

(54) ULTRAVIOLET LIGHT FOR SUMP WATER TREATMENT

(71) Applicant: Nicholas T. Rak, Avon, OH (US)

(72) Inventor: Nicholas T. Rak, Avon, OH (US)

(*) Notice: Subject to any disclaimer, the term of this patent is extended or adjusted under 35 U.S.C. 154(b) by 387 days.

(21) Appl. No.: 17/670,429

(22) Filed: Feb. 12, 2022

Related U.S. Application Data

(60) Provisional application No. 63/187,430, filed on May 12, 2021, provisional application No. 63/167,002, filed on Mar. 27, 2021.

(51) Int. Cl.
*A61L 12/10* (2006.01)
*C02F 1/32* (2023.01)
(Continued)

(52) U.S. Cl.
CPC .............. *C02F 1/325* (2013.01); *A61L 12/10* (2013.01); *F04B 53/22* (2013.01);
(Continued)

(58) Field of Classification Search
CPC .................. C02F 1/325; C02F 2103/06; C02F 2201/3221; C02F 2201/326; C02F 2303/04; C02F 1/008; C02F 1/32; C02F 2201/32; C02F 2209/44; A61L 12/10; F04B 53/22; F04B 2207/043
(Continued)

(56) References Cited

U.S. PATENT DOCUMENTS 5,352,357 A * 10/1994 Perry ...................... C02F 3/302
210/903
5,466,367 A * 11/1995 Coate ........................ C02F 3/10
210/295
(Continued)

FOREIGN PATENT DOCUMENTS

| CN | 204781084 U | * | 11/2015 | ........... Y02A 20/108 |
| CN | 106007227 A | * | 10/2016 | ................ C02F 9/00 |
| DE | 10256849 A1 | * | 8/2004 | ................ F24F 3/14 |

OTHER PUBLICATIONS

English Translation of Li Patent Publication CN-106007227-A, published Oct. 2016. (Year: 2016).*
(Continued)

*Primary Examiner* — Joseph W Drodge
(74) *Attorney, Agent, or Firm* — Gugliotta & Gugliotta, LPA

(57) ABSTRACT

A sump sanitizing system is provided including a UV energy source within a sump tank. The UV energy source may be a light bulb or tube that is submersed in the collected groundwater water within the sump tank. The light bulb or tube may be self contained and waterproof, and may utilized light emitting diodes (LED), or other functional similar UV producing mechanism. For new sump installations the system may be integrated within the other operational components and controls utilized for water removal. For aftermarket installations, a UV source may be fixed to or mounted within an existing sump tank in a manner so as to not interfere with the systems other operations. An electrical power supply may be in communication with the UV source. Power may be communicated in a constant manner, or controlled for intermittent operation with a timer or other type of controller.

8 Claims, 1 Drawing Sheet

(51) Int. Cl.
*F04B 53/22* (2006.01)
*C02F 103/06* (2006.01)

(52) U.S. Cl.
CPC .. *C02F 2103/06* (2013.01); *C02F 2201/3221* (2013.01); *C02F 2201/326* (2013.01); *C02F 2303/04* (2013.01)

(58) Field of Classification Search
USPC .......................................................... 417/12
See application file for complete search history.

(56) References Cited

U.S. PATENT DOCUMENTS

| | | | | |
|---|---|---|---|---|
| 6,447,720 | B1* | 9/2002 | Horton, III | ............... A61L 2/10 210/748.11 |
| 11,913,674 | B1* | 2/2024 | Rak | ........................ F16J 15/022 |
| 2005/0247623 | A1* | 11/2005 | Petrone | .................. C02F 3/082 210/619 |
| 2017/0203986 | A1* | 7/2017 | Ervin | .................. B01D 15/361 |

OTHER PUBLICATIONS

English translation of Prahl Publication DE 10256849A1, published Aug. 12, 2004 (Year: 2004).*
English Translation of Patent Publication CN 203781084U, Li et al., published Nov. 18, 2015. (Year: 2015).*

* cited by examiner

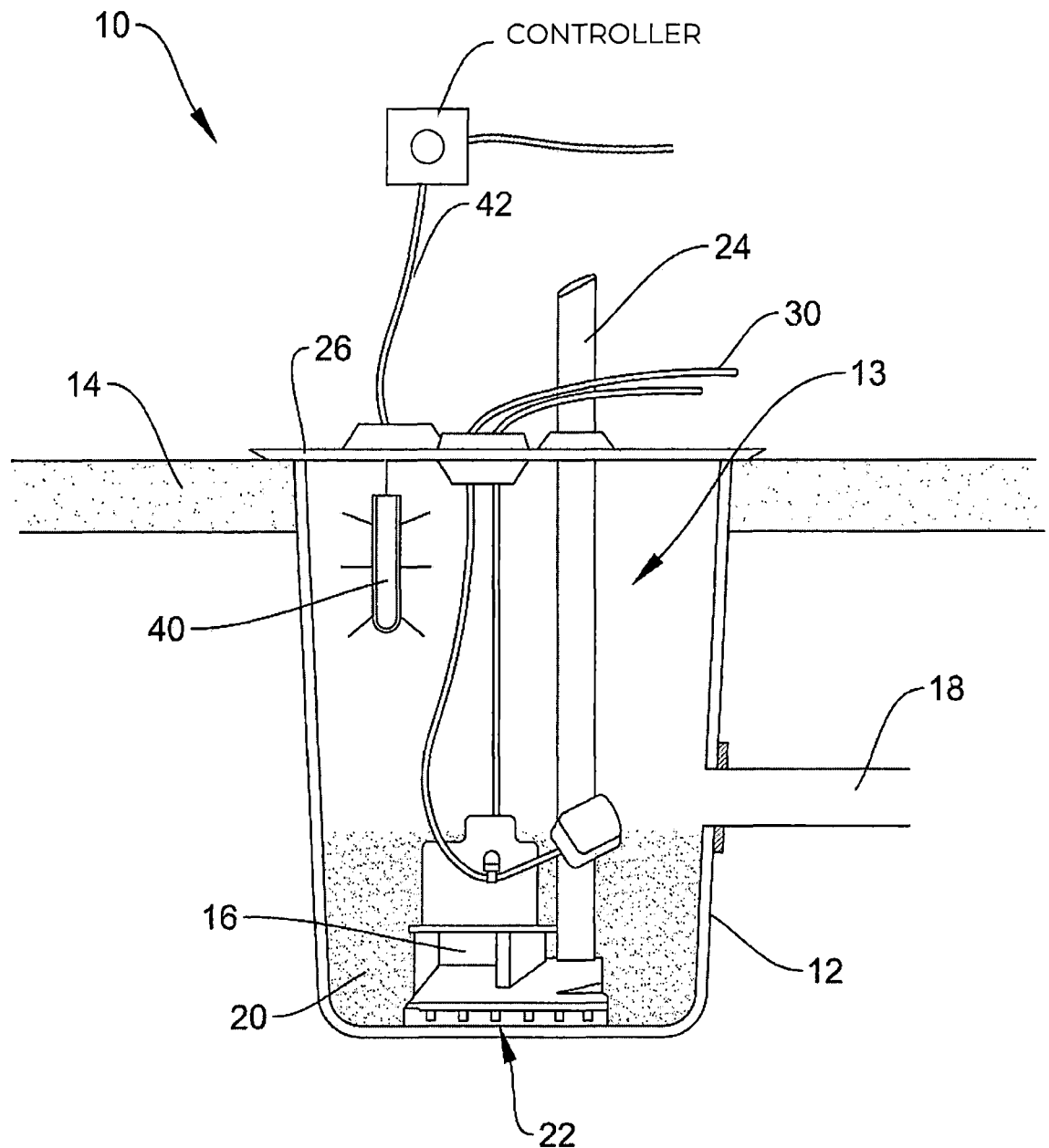

ULTRAVIOLET LIGHT FOR SUMP WATER TREATMENT

BACKGROUND OF THE INVENTION

1. Field of the Invention

The present invention relates generally to improvements to sump pump systems and, more particularly, to a system and method for reducing biological activity within a sump pump system.

2. Description of the Related Art

A sump pump is a pump used to remove water that has accumulated in a water-collecting sump basin, commonly found in the basements of homes. The water may enter via the perimeter drains of a basement waterproofing system, funneling into the basin or because of rain or natural ground water, if the basement is below the water table level.

Sump pumps are generally installed in basements where flooding happens predictably or regularly. The installation is intended to solve dampness where the water table is above the foundation of a home. Sump pumps send water away from a house to any place where it is no longer problematic, such as a municipal storm drain or a dry well.

Whether discharging to the environment or to a storm or sanitary sewer in older installations[1], the installation and operation of such sump pump systems are primarily designed for solving water disposal problems, and modern sump pump components in the United States have become standardized. They consist of: a sump basin of 15 to 25 U.S. gallons capacity in the form of a plastic, metal, or concrete container; and a submersible pump of either ⅓ or ½ horsepower. While such standard designs are generally adequate for the task of removing excess water, some problems can occur during periods of lack of excess groundwater. When the pumps are not operated regularly enough, stagnant water remaining within a sump basin may become an environment that leads to increased mold or bacterial activity that can result in an increase in unpleasant odors.

Such installations may exist in older installations when considered acceptable; however, this practice is now antiquated and may now violate the plumbing codes or municipal laws so as to prevent overwhelming municipal sewage treatment systems.

While there are many water sanitizing products, none are designed for or used in the treatment and maintenance of water within a sump basin.

Ultraviolet Radiation (UVR) is conventionally divided into three bands in order of increasing energy: Ultraviolet-A (UVA), Ultraviolet-B (UVB) and Ultraviolet-C (UVC). This division correspond broadly to the effects of UVR on biological tissue. The common names of UV bands and their respective wavelength ranges, in nanometers, are as follows: UVA: 315-400 nm "Black light"; UVB: 280-315 nm "Erythemal UV"; and UVC: 100-280 nm "Germicidal UV".

Short-wave ultraviolet radiation, in the "C" band (200 to 280 nanometers) has been used for more than 100 years. UV-C (UVC) is also referred to as ultraviolet germicidal irradiation (UVGI). UVC penetrates the outer structure of the cell and alters the DNA molecule, preventing cell replication and causing cell death.

Due to their different wavelengths and energies, each of these bands has distinct effects on living tissue. The highest energy band, UVC, can damage DNA and other molecules and is often used as a germicidal agent. Germicidal lamps, commonly used for sterilization in hospitals, are strong emitters of UVB and UVC radiation. UV light in the form of germicidal lamps has been used since the late 1800's to kill the types of microorganisms that typically cause indoor air quality (IAQ) problems—bacteria, mold, yeast, and viruses. However, to date the use of UV light has not been utilized for or used in the treatment and maintenance of water within a sump basin.

Consequently, a need has been identified for a system and method for reducing biological activity within a sump pump basin utilizing UV radiation.

SUMMARY OF THE INVENTION

It is thus an object of the present invention to provide for the removal or reduction of odors within a sump pump basin.

It is a feature of the present invention to provide for the reduction or elimination of unwanted biological contaminants within the storm/groundwater systems of any structure that has a ground water collection and eliminating system.

According to the preferred embodiment of the present invention, the inclusion of a UV energy source is added within a sump tank. The UV energy source may be in the form of a light bulb or tube that is submersed in the collected groundwater water within the sump tank. The light bulb or tube may be self contained and waterproof, and may utilized light-emitting diodes (LED), or other similar UV producing mechanism (i.e., filament, gas-filled tube, etc.). For new sump installations the system may be integrated within the other operational components and controls utilized for water removal. For aftermarket installations, a UV source may be fixed to or mounted within an existing sump tank in a manner so as to not interfere with the systems other operations. An electrical power supply may be in communication with the UV source. Power may be communicated in a constant manner, or controlled for intermittent operation with a timer or other type of controller.

The operation of the UV source results in the reduction in the uncontrolled growth of mold, algae, bacteria, and fungus (i.e., unwanted biologicals) that may cause an unwanted odor.

It is another advantage of the present invention to improve pump performance by keeping pump intakes and waterways clear of microorganism growth that may impede water flow.

It is yet another advantage of the present invention to reduce or eliminate unwanted biological contaminants within the storm/groundwater systems without significant adverse effects on the ground water effluent.

Further objects, features and advantages of the invention will become apparent in the course of the following description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 1 is a cross sectional schematic of an ultraviolet light system for reducing biological activity within a sump pump system.

DESCRIPTION OF THE PREFERRED EMBODIMENTS

It should be understood that the legal scope of the description is defined by the words of the claims set forth at the end of this patent and that the detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term by limited, by implication or otherwise, to that single meaning. Finally, unless a claim element is defined by reciting the word "means" and a function without the recital of any structure, it is not intended that the scope of any claim element be interpreted based on the application of 35 U.S.C. § 112 (f).

The best mode for carrying out the invention is presented in terms of its preferred embodiment, herein depicted within the FIGURES.

1. DETAILED DESCRIPTION OF THE FIGURES

According to the preferred embodiment of the present invention a system for reducing biological activity, generally noted as 10, is shown according to a preferred embodiment of the present invention. The system 10 generally includes a sump tank 12 or similar lines well that forms a collection volume 13 beneath a floor surface 14. A submersible pump 16 is contained within the collection volume 13. A drain tile or other similar inlet conduit 18 provide for fluid communication between a groundwater source (not shown) and the collection volume 13. Collected groundwater 20 is thereby received into the collection volume 13 and with an inlet 22 of the submersible pump 16. The pump 16 is in fluid communication with a drain pipe 24 forming discharge plumbing. Oftentimes a well cover 26 may seal an upper opening of the sump tank 12. One or more electrical conduits 30 may access form electrical connections for supply power to the pump 16.

A UV energy source, generally noted as 40, is provided within the sump tank 12 and with visual access to the collection volume 13, and especially the collected groundwater 20. The UV energy source 40 may be in the form of a light bulb or tube. The UV energy source preferably generates UVC radiation in the germicidal UV wavelength range of between about 100 nm to about 280 nm. It is similarly preferred that the UV energy source be sufficient to kill bacteria, mold, yeast, and viruses within the collected groundwater 20.

The UV energy source may alternately be submersed within the collected groundwater water 20 within the sump tank 12. The light bulb or tube 40 may be self contained and waterproof. The light bulb or tube 40 may utilized light emitting diodes (LED), or other similar UV producing mechanism such as a filament or gas filled tubes or other functionally equivalent mechanism.

The UV source 40 may be fixed to or mounted to the cover 26 within in a manner so as to not interfere with the operation of the pump. A second electrical power supply 42 may be in communication with the UV source 40.

A controller (not shown) is further anticipated as providing control integration between the operation of the UV source 40 and the submersible pump 16. Power may be communicated in a constant manner, or controlled for intermittent operation with a timer or other type of controller.

2. OPERATION OF THE PREFERRED EMBODIMENT

In operation, the present invention augments the operation of a sump pump 16 in the removal of collected groundwater 20 outward through the drain pipe 24. The pump 16 intakes groundwater from the drain system 14 and moves the groundwater through a pump discharge 24. The UV source 40 is coordinated with the operation of the sump 16 so as to provide germicidal radiation to the collected groundwater 20 and within the collection volume 13. The application of such UV radiation creates an antimicrobial environment within the sump tank 12 for the reduction or elimination of odor forming microorganisms.

According to one aspect of the present invention, the operation of the UV source 40 may be constantly powered. According to another aspect of the present invention, the operation of the UV source 40 may be controlled, and may be controlled in a manner coordinated with either operation of the pump 16 or with presence of collected groundwater 20 within the collection volume 13. By way of example, and not meant as a limitation, the UV source 40 may be activated by a controller for a specific period of time, either at regular intervals or initiated with operation of the pump 16.

The foregoing descriptions of specific embodiments of the present invention are presented for purposes of illustration and description. The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples, and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way. Any unintended embracement of such subject matter is hereby disclaimed. They are not intended to be exhaustive nor to limit the invention to precise forms disclosed and, obviously, many modifications and variations are possible in light of the above teaching. The embodiments are chosen and described in order to best explain principles of the invention and its practical application, to thereby enable others skilled in the art to best utilize the invention and its various embodiments with various modifications as are suited to the particular use contemplated. It is intended that a scope of the invention be defined broadly by the Drawings and Specification appended hereto and to their equivalents. Therefore, the scope of the invention is in no way to be limited only by any adverse inference under the rulings of Warner-Jenkinson Company, v. Hilton Davis Chemical, 520 US 17 (1997) or Festo Corp. v. Shoketsu Kinzoku Kogyo Kabushiki Co., 535 U.S. 722 (2002), or other similar caselaw or subsequent precedent should not be made if any future claims are added or amended subsequent to this Patent Application.

I claim:

1. A method for operating a sump pump system comprising:
   a. collecting groundwater into a sump containment volume having a sump pump;
   b. providing a controller and/or a timer for the system;
   c. sanitizing the collected groundwater using UV radiation in a manner sufficient to reduce or eliminate biological activity within the sump containment volume; and
   d. discharging the sanitized collected groundwater from the sump containment volume through a dedicated discharge outlet of the sump pump system, wherein the UV radiation is applied continuously or intermittently as controlled by the controller and/or timer.

2. The method of claim 1, wherein the UV radiation is provided by a UV-C light source.

3. The method of claim 1, wherein the UV radiation is applied continuously during the collection and discharging of groundwater.

4. The method of claim 1, wherein the UV radiation is applied intermittently based on the detected level of biological activity within the sump containment volume.

5. The method of claim 1, wherein the UV radiation source is positioned one of within the sump containment volume, optionally positioned so as to be submersed, or fixed or mounted to a cover provided for the sump containment volume.

6. The method of claim 1, wherein the sump pump system includes a controller.

7. The method of claim 1, wherein the sump containment volume is sealed by a cover.

8. The method of claim 2, wherein the UV-C light source is configured to emit radiation at a wavelength between 100 and 280 nanometers.

* * * * *